(12) United States Patent
Nageswaran

(10) Patent No.: US 8,227,365 B2
(45) Date of Patent: Jul. 24, 2012

(54) BIOCIDAL CERAMIC COMPOSITIONS, METHODS AND ARTICLES OF MANUFACTURE

(75) Inventor: Ramachandran Nageswaran, Salt Lake City, UT (US)

(73) Assignee: Ramachandran Nageswaran, Salt Lake City, UT (US)

( * ) Notice: Subject to any disclaimer, the term of this patent is extended or adjusted under 35 U.S.C. 154(b) by 1550 days.

(21) Appl. No.: 11/450,034

(22) Filed: Jun. 8, 2006

(65) Prior Publication Data

US 2007/0110824 A1    May 17, 2007

Related U.S. Application Data

(60) Provisional application No. 60/688,506, filed on Jun. 8, 2005, provisional application No. 60/803,703, filed on Jun. 1, 2006.

(51) Int. Cl.
*C01B 7/00* (2006.01)

(52) U.S. Cl. ........ 501/102; 501/103; 501/104; 501/105; 501/106; 423/263; 423/277; 423/306

(58) Field of Classification Search .......... 501/102–106; 423/263, 277, 306
See application file for complete search history.

(56) References Cited

U.S. PATENT DOCUMENTS

| | | | |
|---|---|---|---|
| 4,504,387 A | 3/1985 | LeMire et al. | |
| 4,525,410 A | 6/1985 | Hagiwara et al. | |
| 4,615,705 A | 10/1986 | Scales et al. | |
| 4,775,585 A | 10/1988 | Hagiwara et al. | |
| 4,801,566 A | 1/1989 | Limaye et al. | |
| 4,849,223 A | 7/1989 | Pratt et al. | |
| 4,906,466 A | 3/1990 | Edwards et al. | |
| 4,911,899 A | 3/1990 | Hagiwara et al. | |
| 4,925,816 A | 5/1990 | Watanabe et al. | |
| 4,938,955 A | 7/1990 | Niira et al. | |
| 5,009,898 A | 4/1991 | Sakuma et al. | |
| 5,085,416 A | 2/1992 | Miyake et al. | |
| 5,102,836 A | 4/1992 | Brown et al. | |
| 5,147,686 A | 9/1992 | Ichimura et al. | |
| 5,151,122 A | 9/1992 | Atsumi et al. | |
| 5,180,585 A | 1/1993 | Jacobson et al. | |
| 5,244,667 A | 9/1993 | Hagiwara et al. | |
| 5,296,238 A | 3/1994 | Sugiura et al. | |
| 5,441,717 A | 8/1995 | Ohsumi et al. | |
| 5,488,018 A | 1/1996 | Limaye et al. | |
| 5,503,840 A | 4/1996 | Jacobson et al. | |
| 5,595,750 A | 1/1997 | Jacobson et al. | |
| 5,618,762 A | 4/1997 | Shirakawa et al. | |
| 5,698,229 A | 12/1997 | Ohsumi et al. | |
| 5,753,250 A | 5/1998 | Hagiwara et al. | |
| 5,817,325 A | 10/1998 | Sawan et al. | |
| 5,876,738 A | 3/1999 | Ohno et al. | |
| 6,017,553 A | 1/2000 | Burrell et al. | |
| 6,066,585 A * | 5/2000 | Swartz | .......... 501/128 |
| 6,123,925 A | 9/2000 | Barry et al. | |
| 6,143,318 A | 11/2000 | Gilchrist et al. | |
| 6,200,680 B1 | 3/2001 | Takeda et al. | |
| 6,238,686 B1 | 5/2001 | Burrell et al. | |
| 6,251,417 B1 | 6/2001 | Shiau et al. | |
| 6,264,936 B1 | 7/2001 | Sawan et al. | |
| 6,267,590 B1 | 7/2001 | Barry et al. | |
| 6,350,474 B1 | 2/2002 | Dzneladze et al. | |
| 6,387,832 B1 | 5/2002 | Komarneni et al. | |
| 6,413,895 B1 | 7/2002 | Merkel | |
| 6,423,350 B2 | 7/2002 | Shiau et al. | |
| 6,471,876 B1 | 10/2002 | Hansen et al. | |
| 6,509,057 B2 | 1/2003 | Shigeru et al. | |
| 6,551,608 B2 | 4/2003 | Yao | |
| 6,555,599 B2 | 4/2003 | Lever et al. | |
| 6,576,579 B2 | 6/2003 | Merkel | |
| 6,582,715 B1 | 6/2003 | Barry et al. | |
| 6,605,751 B1 | 8/2003 | Gibbins et al. | |
| 6,715,618 B2 | 4/2004 | Shiau et al. | |
| 6,780,332 B2 | 8/2004 | Shiau et al. | |
| 6,797,278 B2 | 9/2004 | Jackson et al. | |
| 6,897,349 B2 | 5/2005 | Gibbins et al. | |
| 6,921,546 B2 | 7/2005 | Albach | |
| 2002/0099449 A1 | 7/2002 | Speitling | |
| 2004/0214916 A1 | 10/2004 | Patel et al. | |
| 2004/0265350 A1 | 12/2004 | Sambrook et al. | |
| 2007/0221132 A1 | 9/2007 | Chandran et al. | |

FOREIGN PATENT DOCUMENTS

| | | |
|---|---|---|
| CA | 2026535 | 6/2000 |
| EP | 0678548 A2 | 4/1995 |
| EP | 0678548 B1 | 4/1995 |
| GB | 2163346 A | 1/1983 |
| GB | 2134791 A | 2/1984 |
| GB | 2164557 A | 9/1985 |
| GB | 2238044 A | 11/1990 |
| JP | 3193701 A | 8/1991 |
| WO | WO2006/050477 A2 | 5/2006 |

OTHER PUBLICATIONS

S.K.Gogoi et al., Langmuir, [22] pp. 9322-9328 (2006).
R.Kumar and H.Munstedt, J. Biomed Mater Res B Appl Biomater, pp. 311-319 (2005).
E.Uzgur et al., Key Engineering Materials, [264-268] pp. 1573-1576 (2004).
T.N. Kim et al., Journal of Mats. Sc.; Materials in Medicine, [9] pp. 129-134 (1998).

(Continued)

*Primary Examiner* — Steven Bos

(57) ABSTRACT

The present invention provides biocidal ceramic compositions incorporating a bioactive ionic species that is chemically bound in a substantially single-phase, crystalline, [NZP]-type structure, methods for producing the crystalline structures, and articles of manufacture incorporating the crystalline structures, and uses of the articles of manufacture. Bioactive ionic species can be, but are not limited to, Ag, Cu, Ni, Zn, Mn, Sn, Co, H, and combinations thereof.

25 Claims, 4 Drawing Sheets

OTHER PUBLICATIONS

Y. Abe et al., Bioceramics 1st Edition, Ed. By J. Wilson, L.L. Hench and D. Greenspan, pp. 247-251 (1995).
A.D. Russell and W.B. Hugo, Progress in Medicinal Chemistry, [31] Ed. G.P. Ellis and D.K. Luscombe, pp. 351-370 (1994).
N. Grier, Antiseptics and Disinfectants, Ch.18 Ed. S.S. Block, Lea and Febiger, pp. 375-389 (1977).
L. Jinsheng et al., Journal of Rare Earth, vol. 22, No. 3, pp. 436-439 (2004).
1 page from http://web.archive.org/web/20050402103913/http://www.agion-tech.com/ (accessed Mar. 28, 2007).
European Search Report for Application No. EP 06784704, dated Oct. 26, 2009 (published by European Patent Office).
European Search Opinion for Application No. EP 06784704, dated Oct. 26, 2009 (published by European Patent Office).
Office Action of U.S. Appl. No. 11/768,521 dated Jun. 2, 2010.
Office Action of U.S. Appl. No. 11/768,521 dated Nov. 18, 2010.
PCT Written Opinion of the International Searching Authority on International Application PCT/US2006/022478 mailed Sep. 26, 2007.
PCT International Search Report for PCT/US2006/022478 published Nov. 22, 2007 (Published by International Bureau of WIPO).
PCT International Preliminary Report on Patentability of International Application PCT/US2006/022478 issued Dec. 11, 2007.
First Examination Report from Indian Patent Office for Patent Application 221/DELNP/2008 dated May 26, 2011.

* cited by examiner

BIOCIDAL CERAMIC COMPOSITIONS, METHODS AND ARTICLES OF MANUFACTURE

CROSS-REFERENCE TO RELATED APPLICATIONS

This application claims the benefit of and priority to U.S. Provisional Patent Application Ser. No. 60/688,506, filed Jun. 8, 2005, and titled "Biocidal Ceramic Compositions, Methods and Articles of Manufacture," and U.S. Provisional patent Application Ser. No. 60/803,703, filed Jun. 1, 2006, and titled "Biocidal Ceramic Compositions, Methods and Articles of Manufacture," which applications are incorporated by reference herein in their entireties.

GOVERNMENT LICENSE RIGHTS

The U.S. Government has a paid-up license in this invention and the right in limited circumstances to require the patent owner to license others on reasonable terms as provided for by the terms of SBIR Phase I Contract No. NBCHC050032 awarded by Homeland Security Advanced Research Projects Agency.

BACKGROUND OF THE INVENTION

1. The Field of the Invention

The present invention relates to crystalline, substantially single-phase, ceramic compositions incorporating bioactive ionic species that provide biocidal or antimicrobial properties, methods of synthesizing such ceramic compositions and methods for manufacturing microbe-destroying articles using the ceramic compositions and utilizing them.

2. The Relevant Technology

The health and environmental hazards of bacterial contamination from microbes such as *Escherichia coli* and *Salmonella* commonly found in food and water, *Staphylococcus Aureus* present in uncooked or undercooked meat; *Cryptosporidium* parasites found in water, and other such unicellular organisms, are no less than they have ever been in the past. In fact, with increasing human population, growing pollution and the potential threats of bio-terror, microbial problems have assumed greater dimensions in the present day and age.

For centuries, metals such as silver (Ag), copper (Cu), zinc (Zn), tin (Sn) and cobalt (Co) have been known to be benign antimicrobial agents and have been used for various basic microbe-control applications. Most of these applications utilized the antimicrobial metal in its unalloyed or alloyed form. However, in recent times, silver and copper, in particular, have been used extensively in various other forms with other substances for disinfecting (antibacterial, antifungal and antialgal) applications. About 20 years ago, silver began being used with other materials for antimicrobial coatings, components and devices.

Different amounts of bioactive species have been incorporated into various organic, inorganic, composite and porous substrates to facilitate antimicrobial activity or disinfecting properties. Typical conventional uses of silver are based on physical admixing of silver or its compounds (e.g., silver iodide, nitrate, oxide, sulfadiazine) with a carrier for use in topical medications, dentistry and water treatment, or, depositing the mixture on a surface (e.g., colloidal coating, paste, or a glaze) on, for example, textiles, plastics, kitchen counters or tiles for floors and walls in restrooms. However, many of the prior art silver-based compounds contain higher-than-needed levels of bioactive or antimicrobial dopants (Ag, Cu, Zn, etc.) and yet are not capable of sustained, strong antimicrobial activity over a period of time.

In particular, where the antimicrobial species were physically bonded or admixed with the base material or coated onto a substrate, the antimicrobial activity is likely to degrade rapidly resulting from loss of the antimicrobial (Ag, Cu, etc.) species due to dissolution or degradation phenomena. Compared to the relatively unstable organic and composite biocides, inorganic biocides offer the advantages of intrinsically higher environmental stability, safety (non-toxic) and controlled and prolonged antimicrobial activity.

State-of-the-art inorganic antimicrobials such as AgION™ and Zeomic comprise silver (Ag) or copper (Cu) based zeolites (alumino-silicate based minerals), wherein the silver or copper ions are put in place of metal ions in an open, skeletal network structure. However, in this often porous and open structure, both the host metal ions such as sodium ($Na^+$), potassium ($K^+$) and magnesium ($Mg^{2+}$) and the dopant ions such as $Ag^+$ or $Cu^+$ are very loosely held making them vulnerable to rapid, uncontrolled ion-exchange and acid leaching. Additionally, silver ions in such zeolites can be easily reduced to metallic silver which could tend to cause coloring of the antimicrobial material and, in turn, the host object.

Alternative inorganic antimicrobial approaches include antimicrobial compositions based on hydroxyapatite, zirconium/titanium/tin phosphate (such as Alphasan™) or silicon dioxide or titanium oxide or zinc oxide (Microfree™) crystalline chemistry. Several variations of the phosphate based inorganic antimicrobial compositions exist, among which the most exemplary are embodied in U.S. Pat. Nos. 5,296,238, 5,441,717 and 5,698,229. For instance, in U.S. Pat. No. 5,296,238, microbicides cover a family of phosphates represented by the general formula:

$$M_a^1 A_b M_c^2 (PO_4)_d \cdot nH_2O$$

wherein $M^1$ is silver, A represents at least one ion selected from the group consisting of hydrogen ion, alkali metal ions, and ammonium ion, $M^2$ is zirconium or titanium, n represents a number which satisfies $0<n<6$, a and b each represents a positive number and satisfies the equation $la+mb=1$, where l is valence of $M^1$ and m is valence of A, and c is 2 and d is 3.

While these prior-art microbicide (U.S. Pat. No. 5,296, 238) and antimicrobial (U.S. Pat. No. 5,441,717) compositions represent some of the more physically and chemically stable inorganic materials with potentially pronounced and prolonged antimicrobial activity to date, there are shortcomings associated with the intrinsic stability of the above phosphate compositions. The stability issues arise from the presence of monovalent alkali ions present at the A (or $M^1$) site, which creates reactivity and thermal expansion anisotropy issues. C. Y. Huang (Ph.D. Thesis, 1990) has computed and measured the thermal expansion anisotropies—the difference between axial thermal expansions in the 'a' and the 'c' directions of the unit cell—of such compositions and clearly shown the significantly higher anisotropy of the compositions with alkali metal ions (especially, $Li^+$ and $Na^+$) at the $M^1$ or A site as compared to those with the larger alkaline earth ions such as $Ca^{2+}$, $Sr^{2+}$ and $Ba^{2+}$ at these sites.

Notably also, the disclosed synthesis methods for the microbicide and antimicrobial inorganic phosphate compositions of the prior-art discussed above involve: (a) corrosive reagents (chlorides, sulfates, oxynitrates, oxychlorides, etc.) that produce environmentally-unfriendly effluents; and (b) tedious chemistries—sometimes with more than one iteration of digestion with carboxylic or dibasic acids such as oxalic and malic acid, pH-controlled reaction-precipitation, filtration, washing and controlled-drying.

SUMMARY OF THE INVENTION

Ceramic compositions of the present invention are particularly meant to overcome the existing limitations with the stability, reliability and longevity of the state-of-the-art organically or inorganically-based antimicrobial concepts. The present invention provides a way to overcome the above deficiencies with the state-of-the-art and demonstrate crystalline, substantially single-phase, inorganic compositions with excellent antimicrobial properties, environmental (physical, chemical and thermal) stability and high melting temperatures (>1600° C.). The inventive compositions belong to the family of crystalline ceramics called "[NZP]", which encompass numerous sub-families.

By the present invention unique, crystalline, [NZP]-type, inorganic biocidal compositions containing bioactive ions such as, but not limited to, silver, copper and zinc that are chemically-bound in a single-phase crystal structure and yet exhibit excellent antimicrobial attributes by means of controlled ion-exchange or rapid killing mechanisms, and methods to make and use the compositions, are provided. These ceramic biocidal compositions are synthesized with a processing step that includes heat treatment at temperatures >900° C., as a result of which the inventive compositions are inorganic, crystalline and have excellent physical (color, dimensional and microstructural stability), chemical (non-reactive, non-leaching, non-toxic and uniformly bioactive) and thermal (temperature and radiation resistance, low expansion, thermal shock resistant) properties.

Broadly, [NZP] ceramics are represented by the chemical formula $NaZr_2(PO_4)_3$ or $NaZr_2P_3O_{12}$ and characterized by a very unique crystal structure that comprises a three-dimensional skeletal network of $PO_4$ tetrahedra and $ZrO_6$ octahedra which are corner-linked together by shared oxygen atoms. The [NZP] structure is exceptionally flexible towards partial or complete ionic substitution at various lattice sites. [NZP]-type ceramics with alkaline-earth ions substituted at the sodium (Na) site, such as $CaZr_4P_6O_{24}$, $SrZr_4P_6O_{24}$ and $BaZr_4P_6O_{24}$ and certain solid-solutions of the same are significantly more physically, chemically and thermally stable, and mechanically durable than the basic [NZP] compositions with alkali ions at the sodium site (such as $NaZr_2P_3O_{12}$, $Ag_{0.05}Na_{0.95}Zr_2P_3O_{12}$, etc.).

With the above in mind, the materials aspect embodied in the current invention creates novel, crystalline, single-phase, [NZP]-type biocidal compositions which have superior environmental and color stability, high temperature resistance (greater than 1250° C.) and relatively more isotropic structural properties to complement their excellent and reliable antimicrobial performance over prolonged periods compared to the state-of-the-art.

Specifically, the novel biocidal compositions involve: (a) suitable combinations of alkaline earth ($Ca^{2+}$, $Ba^{2+}$, etc.) and bioactive (Ag+, $Cu^+$ or $Cu^{2+}$, $Zn^{2+}$, etc.) ionic substitutions at the sodium (Na) sites and, optionally, any appropriate partial or complete ionic substitutions at other sites, especially the phosphorus (P) site; and (b) any suitable combinations of alkali metal ($Na^+$, $K^+$), alkaline earth ($Ca^{2+}$, $Ba^{2+}$, etc.) and bioactive (Ag+, $Cu^+$ or $Cu^{2+}$, $Zn^{2+}$, etc.) ionic substitutions at the sodium (Na) sites and, necessarily, appropriate partial or complete ionic substitution(s) especially at the phosphorus (P) site.

The synthesis process used to make the crystalline, biocidal compositions of this invention involves less corrosive and hazardous reagents (e.g., carbonates, nitrates, hydroxides and oxides) and, as an added advantage, takes a simpler and direct reaction-precipitation approach followed by calcination (heat-treatment) of the dried precipitate at temperatures between 900° C. and 1200° C.

Overall, the inventive crystalline compositions, by virtue of the myriad ways of doping them with bioactive elements and myriad forms into which they can be made, offer remarkable versatility of use for applications ranging from disinfection of water and contaminated fluids to microbe-proofing of food items and packages, construction materials, textiles and rubber, home and industrial appliances, medical devices, and space suits to enabling catalytically-enhanced oxidation of soot particles in diesel particulate filters (DPFs).

These and other embodiments of the present invention will become more fully apparent from the following description and appended claims, or may be learned by the practice of the invention as set forth hereinafter.

BRIEF DESCRIPTION OF THE DRAWINGS

To further clarify the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF EXEMPLARY EMBODIMENTS

Figure 1:
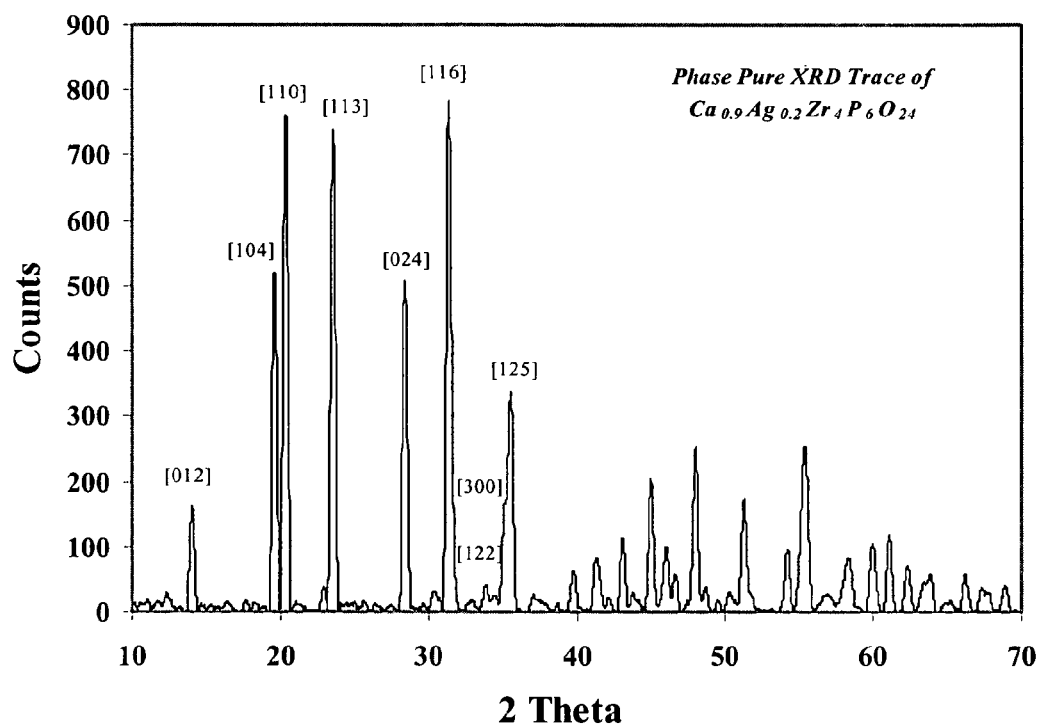
FIG. 1 shows an X-ray diffraction analysis pattern corresponding to one of the crystalline, single-phase [NZP]-type, biocidal Type (I) ceramic compositions.

The present invention relates to biocidal, crystalline, [NZP]-type ceramic compositions having an effective amount of active species incorporated in the crystal structure to form substantially single-phase compositions (hereinafter, referred to as "ceramic compositions" or "single-phase compositions"), methods for producing such ceramic compositions, as well as uses for the ceramic compositions of the present invention. As used herein, the term "substantially single-phase composition" refers to the incorporation of the bioactive agents into the crystalline ceramics such that chemical bonding of the bioactive agent occurs at the atomic level with the crystalline structure. One way this is represented is that single-phase compositions have chemical formulas such as '$Ca_{1-x}Ag_{2x}Zr_4P_6O_{24}$' where 'x' can assume values from 0 to 1, whereas multi-phase compositions have chemical formulas denoted as, for example, $Ag_2O+SiO_2$, $AgNO_3+TiO_2$, Ag+HAP, etc. FIG. 1 shows the X-ray diffraction pattern of an inventive single-phase composition with chemical formula $Ca_{0.9}Ag_{0.2}Zr_4P_6O_{24}$.

Chemically bonding the antimicrobial element to the ceramic crystal structure extends the antimicrobial life of the material since the chemical bond increases the retention of the bioactive agent within the ceramic structure and prevents leaching of the element therefrom as typically occurs in many of the prior art ceramic materials having silver or silver-based anti-microbial agents. In some of the prior art, antimicrobial elements could be leached away by the environment, for example via hot water, dilute hot acids and alkalis or deteriorate due to significant heat. In these prior art compositions, when exposed to heat, the silver could dissociate from the host carrier or matrix (especially, in the case of polymeric hosts such as resins, nylon, polyester, polyurethane, etc.) that decomposes, ablates or melts away. Therefore, in single-phase compositions, the bioactive agent is essentially locked in the chemical structure reducing its ability to be removed from the ceramic composition, except by selective and controlled ion-exchange, and maintaining its effectiveness over even longer periods of time than is possible in the prior art.

The ceramic compositions of the present invention relate to a large family of ceramics generally known as [NZP]s whose crystal structures are characterized by a three-dimensional network of corner-linked polyhedra ($PO_4$ tetrahedra and $ZrO_6$ octahedra) having rhombohedral or monoclinic crystal symmetries.

Generally, the ceramic compositions of the present invention, will have a single-phase crystalline structure. For example, those of skill in the art will understand that individual [NZP]-type crystallites inherently always has a single-phase structure. However, when the [NZP]-type ceramic compositions are synthesized, all of the bioactive species may not necessarily react to form the single-phase ceramic composition. Thus, compositions of the present invention have at least 90% of the bioactive species chemically bound to the single-phase crystalline structure, preferably at least 95% of the bioactive species chemically bound to the single-phase crystalline structure, even more preferably at least 99% of the bioactive species is chemically bound to the single-phase crystalline structure. Also, in spite of the use of high purity raw materials, it is possible that a small portion of the reactants may stay unreacted or partially reacted and present themselves as separate phases. Based on X-ray diffraction analysis, it has been determined that a nominally phase pure [NZP] composition, in crystalline powder form, still has about 5.0 volume % of non-[NZP] phases. In spite of the small amounts of non-[NZP] phases, many [NZP] compositions have excellent chemical and thermal stability, and melting points in excess of 1500° C. For the purposes of clarity, as used herein, the term "substantially single-phase" accounts for possible situations where extraneous phases may appear in the [NZP] compositions, whether they are in as-synthesized powder form or as-processed bulk articles.

A unique and extremely advantageous feature of the [NZP] structure is that it is exceptionally flexible towards partial or complete ionic substitutions at various lattice sites. The chemical formula for the basic or parent [NZP] composition is $NaZr_2P_3O_{12}$ and a generalized formula representing the stoichiometry of such [NZP] compounds is $M^1M^2A_2^{VI}P_3^{IV}O_{12}$, where $M^1$ is typically referred to as "sodium" site and $M^2$ notates any substitutions for or excess additions at the $M^1$ site. If the valency of the cation occupying the $M^1$ site is '2' (alkaline earth ion), then the general formula becomes $M^1M^2A_4^{VI}P_6^{IV}O_{24}$, where $M^2$ represents substitutions or excess additions to the $M^1$ site.

The inventive ceramic compositions herein are represented by the following general chemical formulas where $M^2$, A and B represent the respective ionic substitutions at the parent $M^1$, Zr (zirconium) and P (phosphorus) host sites of the [NZP] structure:

(I) $M^1_{1-x-jy-mz}M^2_{kx}Zr^{VI}_{4-y}A_yP^{IV}_{6-z}B_zO_{24}$, where '$M^1$' can be one or more divalent alkaline earth cations such as Mg, Ca, Sr, Ba, or a stoichiometric combination thereof; '$M^2$' can be any bio-active element such as, but not limited to, H, Ag, Cu, Ni, Zn, Mn, Co, or a stoichiometric combination thereof, and x, y, z, k, j, and m are governed by the following mathematical rules:
  (i) $0 < 'x' \leq 1$, $0 \leq 'y' \leq 4$, and $0 \leq 'z' \leq 6$, wherein $(jy+mz) < (1-x)$;
  (ii) 'k'=1 if '$M^2$' is a divalent cation such as $Cu^{2+}$, $Ni^{2+}$, $Zn^{2+}$, and the like, or a stoichiometric combination thereof;
  (iii) 'k'=2 if '$M^2$' is a monovalent cation such as $Ag^+$, $Cu^+$, and the like, or a stoichiometric combination thereof;
  (iv) 'j'=0.5 or 0 or –0.5, respectively, depending on whether 'A' is pentavalent (such as, but not limited to, $Nb^{5+}$, $Ta^{5+}$, $V^{5+}$, and pentavalent lanthanide metals) or a tetravalent (such as, but not limited to, $Ti^{4+}$, $Hf^{4+}$, and tetravalent lanthanide metals) or a trivalent (such as, but not limited to, $Y^{3+}$, $Sc^{3+}$, and trivalent lanthanide metals) cation; and
  (v) 'm'=0.5 or 0 or –0.5 or –1, respectively, depending on whether 'B' is hexavalent (such as $S^{6+}$) or pentavalent (such as $As^{5+}$) or tetravalent (such as $Si^{4+}$, $Ge^{4+}$) or trivalent (such as $Al^{3+}$, $B^{3+}$) cation;

(II) $M^1_{1-x-jy-mz}M^2_{kx}Zr^{VI}_{2-y}A_yP^{IV}_{3-z}B_zO_{12}$, where '$M^1$' is one or more monovalent alkali cations such as Li, Na, K, Rb, Cs, or a stoichiometric combination thereof; '$M^2$' can be any bio-active element such as, but not limited to, H, Ag, Cu, Ni, Zn, Mn, Co, or a stoichiometric combination thereof, and x, y, z, k, j, and m are governed by the following mathematical rules:
  (i) $0 \leq 'x' \leq 1$, $0 \leq 'y' \leq 2$, and $0 < 'z' \leq 3$, wherein $(jy+mz) < (1-x)$;
  (ii) 'k'=0.5 if '$M^2$' is a divalent cation such as $Cu^{2+}$, $Ni^{2+}$, $Zn^{2+}$, and the like; or a stoichiometric combination thereof;
  (iii) 'k'=1 if '$M^2$' is a monovalent cation such as $Ag^+$, $Cu^+$, and the like, or a stoichiometric combination thereof;
  (iv) 'j'=1 or 0 or –1, respectively, depending on whether 'A' is pentavalent (such as, but not limited to $Nb^{5+}$, $Ta^{5+}$, $V^{5+}$, pentavalent lanthanide metals) or a tetravalent (such as but not limited to, $Ti^{4+}$, $Hf^{4+}$, tetravalent lanthanide metals) or a trivalent (such as, but not limited to, $Y^{3+}$, $Sc^{3+}$, trivalent lanthanide metals) cation; and
  (v) 'm'=1 or 0 or –1 or –2, respectively, depending on whether 'B' is hexavalent (such as $S^{6+}$) or pentavalent (such as $As^{5+}$) or tetravalent (such as $Si^{4+}$, $Ge^{4+}$) or trivalent (such as $Al^{3+}$, $B^{3+}$) cation.

Exemplary formulas according to the above general formulas include, but are not limited to, $Ca_{0.9}Ag_{0.2}Zr_4P_6O_{24}$ and $SrNi_{0.1}Zr_{3.9}Y_{0.1}P_{5.9}Si_{0.1}O_{24}$ from Type (I) ceramics, and $KNi_{0.1}Zr_2P_{2.8}Si_{0.2}O_{12}$ and $NaAgZr_2P_2SiO_{12}$ from Type (II) ceramic compositions.

One important aspect of this invention is the ionic-doping of the ceramic compositions with effective amounts of a bioactive agent usually substituting at the appropriate sites (as discussed earlier) of the [NZP]-type crystal structure. The bioactive agent can be a bioactive antimicrobial element, e.g., for killing bacteria, microbes, or algae, or may have another property, such as a catalytic or chemical conversion property. In one embodiment, bioactive agents include but are not limited to, Ag, Cu, Zn, Ni, Mn, Co, or other metallic elements. In addition, the bioactive agent could potentially be hydrogen (H). The bioactive agent can be incorporated in various concentrations, for example, in amounts of about 0.0001 to about 20.0 wt % of the single-phase ceramic composition. In another important embodiment, the 'A' atoms substituting at the octahedrally-coordinated (VI) zirconium (Zr) sites, can include lanthanide metals. Another noteworthy embodiment is that, where the phosphorus (P) ions at the tetrahedrally-coordinated (IV) phosphorus site themselves can have antimicrobial activity, this adds to the antimicrobial activity of the ceramic composition as a whole. However, doping the ceramic composition with any bioactive agent as described above has a synergistic effect above and beyond the inherent antimicrobial activity of the inorganic complex-phosphate material itself Because the M sites can be adjusted to have various alkali or alkaline earth elements, different elements (ions) can be substituted and the compositions can be tailored appropriately for each application. For example, in one embodiment of the present invention, the $M^1$ site can be calcium (Ca). Calcium-based ceramics, especially phosphates, are unique because they are extremely biocompatible. Therefore, bio-applications involving the human body and life-sustaining utilities, may be calcium-based, single-phase [NZP]-type compositions such as, but not limited to, $Ca_{0.95}Ag_{0.1}Zr_4P_6O_{24}$. The relevant bio-applications cover a broad range from medical devices such as, but not limited to, catheters, feeding tubes, woundcare ointments, dental cements, and non-biofouling membranes for disinfection of drinking water or wastewater.

However, any or all of M (alkali or alkaline earth), Zr (zirconium) and/or P (phosphorus) sites can be manipulated to engineer single-phase [NZP] or [NZP]-type compositions with desirable properties. For example, for applications where a stronger and more thermally stable, UV-stable, and/or mechanically stronger bioactive ceramic material is desired, barium-based polycrystalline, single-phase compounds, such as, but not limited to, $Ba_{1.3}Zr_{3.9}Co_{0.1}P_{5.6}Si_{0.4}O_{24}$, may be more preferred—where, the bioactive element is 'Co'. As such, the ceramic compositions can also be modified as desired to increase their stability and to have enhanced chemical properties.

In another useful embodiment of the invention, silicon ('Si') substitution of the $P^{IV}$ site can substantially improve the environmental (due to moisture, salts, reducing agents, etc.) and discoloration resistance of the ceramic compositions. For instance, a ceramic composition having the formula $KAg_{0.1}Zr_2P_{2.9}Si_{0.1}O_{12}$ is expected to have better environmental and color stability than, for example, $K_{0.9}Ag_{0.1}Zr_2P_3O_{12}$ especially at higher temperatures and in the presence of light or radiation. A few common and important features of the ceramic compositions, especially those with silica-substitution, of the present invention is that they are insoluble in water and non-polar solvents, chemically inert against corrosive species such as acids, alkalis and salts to temperatures greater than 100° C., stable up to very high temperatures in air (at least 1400° C.), and, more notably, substantially harmless to the surrounding environment (human bodies, animals, plants, etc.).

Yet another exemplary embodiment of the invention is producing single-phase crystallites which can be formed into various morphologies such as powders (e.g., particulates and grains), whiskers, fibers, and the like, such that the bioactive agent is incorporated substantially evenly throughout the crystalline structure and across all crystallites. The present invention allows for doping the ceramic composition in a more homogeneous or uniform manner than was possible in the prior art. The ceramic crystallites have a substantially uniform concentration of bioactive agent throughout so that in any cross section of the ceramic body the antimicrobial effectiveness is virtually the same. As such, a user of a bulk structure or product formed from ceramic crystallites of any given composition and in any application, especially in bio-applications, can be assured of effectiveness across the entire structure. For example, where the ceramic crystallites are formed into a bulk object such as a monolithic water purifier or filter, the entire structure will have substantially the same biological activity throughout so that portions of water will not go untreated or less treated. Moreover, the presence of controlled porosity increases the surface available for biocidal activity. Thus, where ceramic structures of the present invention include bioactive agents, the monolithic ceramic structures have the highly desirable properties of isotropic, stable, controlled and prolonged ion-exchange based antimicrobial characteristics.

The ceramic compositions of the present invention are amenable to varying and/or controlling the doping levels of the bioactive agent(s). Depending on the application, a higher concentration of bioactive agent may be desired. For example, in waste water treatment facilities where water flow rates and volumes are relatively high, the concentration of the antimicrobial agent (such as silver 'Ag') in the water filters may be higher than for filters for point-of-service water purifiers, for example, tap water. A combination of bioactive agents may also be desired. For instance, in wastewater filtration applications, it may also be desirable to control the growth of algae. Accordingly, the ceramic compositions may have, for example, both silver ('Ag') and copper ('Cu') as bioactive agents present in the single-phase [NZP] structure.

Another manifest advantage of the biocidal ceramic formulations of the present invention is that the formulations are also capable of destroying microbes virtually upon contact—referred to as "pseudo contact-killing". This occurs when a sufficiently high concentration of very-finely dispersed submicron or nano-sized grains of the antimicrobial [NZP]-type composition is utilized, whether in the form of a mixture with a non-leachable organic or inorganic carrier, or as in a coating layer on the surface of any article or device, or as incorporated into a bulk object made from the antimicrobial compound. At optimum grain size, concentration and type of bioactive agents, the resulting rapid rates and larger surface of activity of the ion-exchange based microbe destruction process produces substantially the same effects as contact-killing.

Various synthesis techniques based on wet-chemical methods such as sol-gel, and hydrothermal synthesis, and dry techniques such as solid state reaction (or oxide-mixing) can be used for making the inventive ceramic compositions. For example, in the sol-gel synthesis embodiment, the raw materials employed are water soluble salts (e.g., chlorides and nitrates) of alkali or alkaline earth element(s) and the bioactive element(s) like silver, copper and zinc, zirconium complexes such as zirconium oxychloride, $(ZrOCl_2 \cdot xH_2O)$ and oxynitrate $(ZrO(NO_3)_2 \cdot xH_2O)$, and ammonium dihydrogen phosphate $(NH_4H_2PO_4)$ or phosphoric acid $(H_3PO_4)$. As desired, predetermined and controlled amounts of silicon ions can be introduced in place of phosphorus ions, by mixing the aqueous solution containing the alkali/alkaline earth species and $Zr^{+4}$ ions with silica $(SiO_2)$ sol followed by addition of a solution containing phosphorus ions. Upon addition of the phosphorus containing species, a gel-like precipitate results. The precipitate is dried in air at 100° C. for 24 hrs. and then crushed and ground using a mortar and pestle, or other suitable methods, to yield fine agglomerated powder. The fine powder is then calcined at temperatures between 750° C. and 1050° C. for about 5-10 hours to obtain crystalline, single phase [NZP]-type antimicrobial compositions.

The hydrothermal technique, a technique similar to that used for sol-gel, can be used to produce precursor powders of the inventive compositions which are then treated hydrothermally under controlled pH conditions to obtain single phase ceramic compositions, for example, $Ca_{0.95}Ag_{0.1}Zr_4P_6O_{24}$. As in the case of the sol-gel method, to ensure complete crystallinity and single-phase nature of the compositions, post-heat treatment (between 800° C. and 1000° C.) of the hydrothermally-derived powders may be necessary.

In utilizing the solid-state oxide reaction synthesis process, different precursors may be used. In one embodiment, for Type (I) compositions, a stoichiometric mixture of zirconates of the alkaline-earth metal along with oxides, carbonates or hydroxides of the bioactive elements, zirconium pyrophosphate ($ZrP_2O_7$) and silica ($SiO_2$) can be used to obtain single-phase compositions such as $Ba_{1.3}Zr_{3.9}CO_{0.1}P_{5.6}Si_{0.4}O_{24}$ through solid-state mixing and reaction calcination at temperatures as high as 1200° C. For optimum results from the solid-state calcination process, the precursors should be mixed thoroughly for which any suitable method may be used. In one advantageous embodiment, grinding is performed by ball milling with ceramic grinding media for convenience and reliability.

Figure 2:
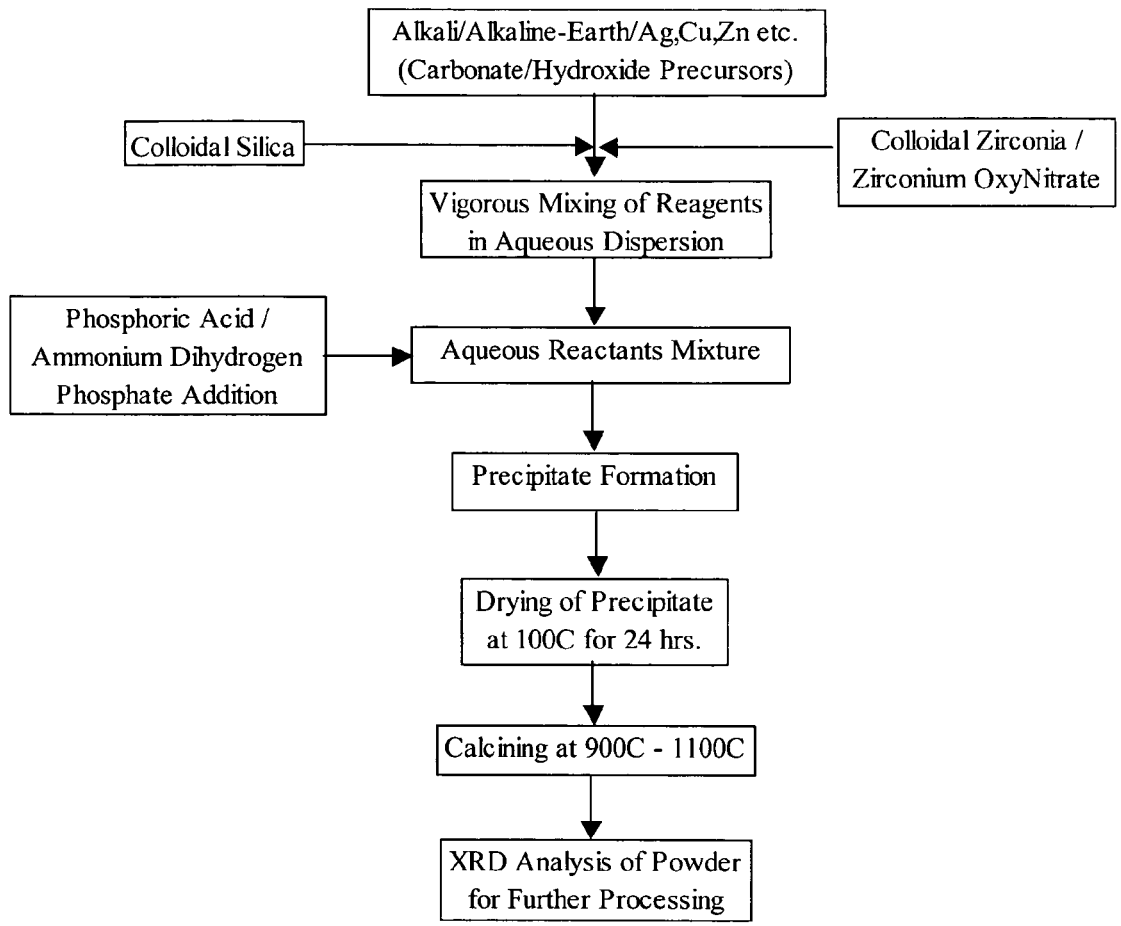
FIG. 2 illustrates a flow chart of the sequence of processing steps for synthesizing the inventive ceramic compositions into powder form using the environmentally-safer, reaction-precipitation based wet-chemical approach, according to one aspect of the present invention.

One preferred and beneficial embodiment of the processing approach(es) to synthesize the inventive ceramic compositions involves a simple, more environmentally-safe reaction-precipitation approach, in which the preferred chemical reagents: are carbonates, nitrates, acetates, hydroxides or oxides, any of which can be used as a raw material source to provide the alkali, alkaline earth, bioactive species, and/or the zirconium or species substituting for the zirconium site. In addition, chemical reagents can include phosphoric acid ($H_3PO_4$) or ammonium dihydrogen phosphate ($NH_4H_2PO_4$) that can be used as a raw material to provide the phosphorus species. Colloidal silica can be used when silicon substitution of phosphorus in the ceramic compositions is targeted. All chemical reagents, except the phosphate species, are first intimately mixed into a slurry with finely divided solids dispersed in an aqueous medium. Intimate mixing is accomplished with the help of ceramic grinding media and suitable mixing action such as rolling or vibration. The calculated amount of phosphoric acid or ammonium dihydrogen phosphate, preferably at a temperature between 35° C. and 40° C., is then slowly added to the aqueous slurry accompanied by steady stirring of the reaction mix. After reaction, fine inorganic precipitates, with a paste-like consistency, of the respective ceramic compositions are formed. This paste is dried at about 100° C. for about 24 hours or until completely dry. The dried amorphous or partially-crystalline precipitates are calcined (heat-treated) between 900° C. and 1200° C. (depending on composition) to obtain crystalline and single-phase compositions. A flow chart of the reaction-precipitation processing approach related to the inventive compositions is provided in FIG. 2. As can be noted, this process is similar to the sol-gel approach except that it utilizes fine dispersions or colloids instead of sols (solutions) for the reactants. Single phase and crystalline nature of the compositions is verified using X-ray diffraction (as shown in FIG. 1) analysis and particle density measurements followed by comparison with theoretical values.

Since the biocidal ceramic compositions of the present invention are expected to show excellent antimicrobial properties in addition to being physically, chemically and thermally very stable, appropriate testing was undertaken to demonstrate the same. To test the biocidal properties of the inventive compositions, conventional or modified assays based on AATCC or EPA protocols can be adopted. Whether in aqueous powder formulations or as bulk test samples, log kill rates after 24 hours test exposure with respect to *Salmonella cholerasuis* and (or) other commonly found harmful microbes such as *Escherichia coli* and *Staphylococcus aureus* need to be adequately high. Log kill rates of greater than 1.0 or 2.0 using standard antimicrobial assay procedures are considered to be high enough for various applications in the field. As discussed in detail in Examples 2 and 4 (below), the log kill rates of the inventive concepts were measured to be exceptionally high compared to various state-of-the-art antimicrobial concepts. As provided in the examples, all the [NZP]-type biocidal compositions (in powder or bulk form) of the present invention exhibit log kills rates of at least 1.0 with respect to *Salmonella* cholerasuis and *Escherichia coli* under standard assay testing. In another embodiment, in the same tests, several [NZP] compositions exhibited extremely high log kill rates of over 5.5, reproducibly. In yet another embodiment, the log kill rate for a few of the inventive [NZP]-type compositions is about 1.0 to about 7.0, preferably up to about 7.0. In addition, Example 5 below establishes non-leaching, non-discoloring and environmental resistance characteristics of the ceramic compositions.

The ceramic compositions of the present invention can be very advantageously utilized for antimicrobial applications in various material forms. As used herein, the term "material" covers any morphology wherein substantially the entire morphology comprises crystallites of the inventive ceramic composition. Thus, materials of the present invention can include, but are not limited to, powders, bulk objects, and the like, that incorporate crystallites according to the compositions of the present invention, wherein the crystallites are substantially single-phase. In one embodiment, crystallites can be manufactured directly in powder form, and utilized in powder-laden plastics or rubbers, powder-mixed fertilizers or other chemicals, powder-containing cosmetics and dispersions, powder-containing papers, and powder-coated textiles. In another embodiment, when powders of the biocidal compositions are mixed with appropriate organic and inorganic dispersants (phosphates, sulfonates, polyacrylates, etc.) and binders (silicates, glycols, starches, and the like) to produce paintable or sprayable mixtures they can be conveniently and beneficially utilized for coating the interior of buildings, walls, home and office furnishings, sewer or storm drain pipes, textiles and apparel, leather and sporting goods, filters for water or air or gases, packages for food and other perishables, bones and cartilages etc. Powder-based coatings are also capable of being applied to various large substrates or surfaces ranging from kitchen, bathroom or masonry tiles to exteriors of buildings and bridges, automobiles, aircraft and marine vehicles using suitable techniques ranging from glazing and sputtering to combustion and plasma spray processes.

It is also a notable aspect of this invention that the size of the grains in the powder can be modified to include nano-sized particles, which enables the realization of thin-film coatings with rapid microbial destruction (pseudo contact-killing) properties that are advantageous and appropriate for bones and cartilages, medical devices, clean-room facilities in hospitals and electronics, and space-suits and other space-related modules that must be protected from microbial contamination. On the other hand, large-grained powders (resembling sand or grog or, even small rocks) of the inventive biocidal ceramic compositions have great applicability in disinfection treatment of contaminated liquid streams, particularly so, for waste-water and drinking water. The powder form of the respective compositions includes any suitable morphologies such as, but not limited to, platelets, whiskers, fibers, and the like, depending on the particular application for which they will be used.

In another aspect of the utility of this invention, appropriately sized and shaped single-phase ceramic compositions can be used as antimicrobially-active fillers or sealants admixed with: (1) organic material carriers such as, but not limited to, natural or synthetic resins, epoxies, plastics, polymers, rubber, wood pulp, etc.; or (2) inorganic carriers comprising various cements (natural, Portland, dental, and such), plasters (gypsum, dolomite, etc.), resins (polysilzanes, polycarboxysilazanes, etc.) and substrates (glassy matrices, silica or other aerogels, zeolites, activated charcoal, etc.); or (3) in mixtures of any of the above organic and inorganic carriers.

For producing bulk components from the single-phase biocidal ceramic compositions, any known shape forming technique such as die and iso pressing, slip casting, extrusion, and injection molding can be used. All green bodies are subjected to carefully controlled drying, debindering, and sintering schedules—with the schedules having a dependence on size, shape and desired final properties of the bulk article. In general, in the bulk article processing approach, pre-qualified powders of the inventive compositions are milled or screened to obtain a particle size distribution that is appropriate for the process. Organic or inorganic surfactants and binders such as, but not limited to, polyacrylates, sulfonates, sodium silicate, stearic acid, paraffin wax, polyethylene glycol (PEG), polyvinyl buterol (PVB), and polyvinyl alcohol (PVA) are added in the amounts of a few weight percent based on solids to improve the formability and green strength of the component. The material is then cast or formed into a desired shape.

Using the above methods or other methods understood to those of skill in the art, ceramic structures can be formed in myriad sizes and shapes. Alternatively, sizing and shaping of the ceramic structures can be part of an additional step subsequent to forming and sintering the bulk ceramic structure. A specific instance of a post-processing step is machining. Typically, the bulk ceramic object is formed and consolidated to a shape and size that are as close to final requirements as possible and then machined to exact final shape and size. As will be appreciated, the potential uses of bulk ceramic structures based on the biocidal compositions of the present invention are many. Among the many ceramic objects producible, one of the more desired embodiments for antimicrobial application is that of a water filter. The use of ceramic filters has been found to be significantly more advantageous. Ceramic filters have the intrinsic properties of non-toxicity, corrosion resistance, high temperature resistance, ability to handle large pressure drops, diminished fouling, excellent control of porosity and pore size distribution, and rigidity to allow manifolding.

Depending on the design and functionality of the filter, its shape and size can vary from a simple circular disk about 7.62 cm (about 3 inches) in diameter by about 0.635 cm (about 0.25 inches) thick to a complex, multichannel rectangular or tubular shape several centimeters in cross section and tens of centimeters in length. Typically, the simple disk-shaped ceramic filters can be formed by pressing appropriate powders of the ceramic composition mixed with a suitable amount of binder and/or fugitive binder in a die under a uniaxial hydraulic press at about 40 to 55 MPa pressure, followed by cold isostatic pressing at about 200 MPa. After the isostatic pressing, the component is heated slowly in a furnace up to the binder burnout temperature and then further up to the sintering temperature anywhere between 1400° C. to 1600° C. for several hours to densify the ceramic to required levels and retain porosity appropriate for filtration purposes. Relatively more complex-shaped, larger filters can be fabricated using wet-methods such as slip casting and pressureless sintering. Aqueous slip-casting is a cost-effective, manufacture and environmental-friendly process that yields objects with uniform physical, chemical and mechanical properties.

Another uniquely beneficial aspect of this invention is that filters (for fluids such as, but not limited to, water and gases) made out of the inventive antimicrobial ceramic compositions can be made to simultaneously and advantageously perform microbial decontamination (biological purification) and ultrafiltration (physical purification). Knowing the excellent antimicrobial properties of the inventive ceramic compositions and having the ability to form a chemically inert, non-leaching filter body of any desired shape and size, it is then only a matter of tailoring the porosity in the surface and bulk of the filter body so that it enables ultrafiltration without reducing the efficiency of the filtration process. Therefore, two advantageous results of the application include a high surface-to-volume ratio filter design, and adequate physical and mechanical properties of the filter.

To obtain the dual-purpose, high performance filter geometries from the ceramic compositions of this invention, the microstructure and porosity aspects of the filter body can be carefully controlled. It has been noted that introducing porosity whose nominal size ranges from about 0.5 to about 0.9 microns makes the filter "bacterially-safe" and, furthermore, "bacterially-sterile" when the pores are nominally between about 0.2 to about 0.5 microns. In one embodiment, the porosity of the ceramic structure is controlled by choosing crystalline feedstock with the appropriate particle size distribution. In another embodiment, porosity characteristics are tailored by introducing pore-formers in various ways and/or by refining a few of the processing steps downstream. With respect to ultrafiltration aspect of the inventive dual-purpose filter concept, in one embodiment, the porosity is about 0.005 to about 0.25 microns at least on the very surface (membrane layer) of the filter. In another embodiment, the ultrafilter configuration includes a gradual porosity gradient from the surface of the filter to the interior. This can be achieved conveniently by fabricating a multi-layer pore structure. The macro-sized porosity can reside in the bulk (interior portion) and submicron or nano-pores at the surface (exterior portion) with micropores in the region in between.

As mentioned earlier, the ceramic compositions as well as the bulk ceramic structures made from them are stable up to high temperatures. This can be advantageous in many scenarios as is elucidated in the following. Typically, in filtration applications, the pores of the ceramic filter tend to get clogged over a period of time in service and must be declogged or regenerated quickly to avoid down time during filter cleaning via conventional means such as back-pulsing, steam cleaning, vacuuming or by baking out the undesired material. However, because the ceramic compositions of the present invention are stable at high temperatures, have very low thermal expansion and very high thermal shock resistance, and are good microwave absorbers, the ceramic filters can potentially be regenerated in situ. A material's ability to absorb microwaves is dictated by its dielectric constant—materials with large dielectric constants are good absorbers of microwave energy. Materials which are microwave absorbers are well known in the art (e.g., EP 420513-B1) and several [NZP] compositions are notable among them. In particular, Type (II) inventive compositions which are analogous to $Na_{1+x}A_2{}^{VI}P_{3-x}{}^{IV}Si_xO_{12}$ (where value of 'x' is greater than 0) result in excellent microwave coupling, for values of x between 1.0 and 2.2, and they also exhibit ultra low (or negative) coefficient of thermal expansion and good thermal shock resistance.

Thus, in one embodiment, a microwave non-absorbing bulk body housing the microwave suscepting ceramic filter can be placed in a microwave and the filter heated and unclogged. In yet another embodiment, the inventive composition of the ceramic filter has the ability to support catalytic oxidation of carbonaceous material in the presence of heat. As a result, the filter regeneration can take place at a relatively lower temperature and the efficiency of the in-situ filter regeneration process is likely to be significantly improved In yet another embodiment, as the ceramic composition is durable against environmental phenomenon and heat, the ceramic filter could be regenerated using high temperature and high pressure steam without the concern of leaching of the antimicrobial elements.

The ceramic compositions and/or materials of the present invention can be applied to applications other than biocidal or antimicrobial applications but which require the characteristics of the ceramic compositions of the present invention which are, but are not limited to, (1) compositional flexibility, (2) a crystalline ceramic structure; (3) excellent stability at extreme temperatures; (4) chemical inertness and non-toxicity; (5) controlled concentration of an active element, such as a bioactive element or other such elements, introduced into the ceramic structure by ionic-substitution; (6) custom-formability into various particle morphologies and as bulk objects, (7) controlled porosity of the ceramic object all through the bulk; (8) engineered properties for multifunctionality; and (9) other characteristics that would be understood by those skilled in the art such as, but not limited to, reduced weight, high strength and high toughness.

The following non-limiting examples are presented to explain the present invention in further detail.

EXAMPLES

Synthesis of Biocidal Ceramic Compositions

Example 1

As discussed earlier and depicted in the flow chart of FIG. 2, a reaction-precipitation wet chemical method was used for synthesizing all the substantially single-phase, crystalline [NZP]-type biocidal compositions. Batch sheets and formulations were prepared first with the objective of obtaining at least 250 gms. each of specific compositions of Type (II) and Type (I), some of which are listed in Table 1. The batch formulations were based on the use of carbonate or hydroxide or oxide or nitrate reagents, or combinations thereof, and phosphate compounds for the wet chemical synthesis approach.

TABLE 1

| Sample Designation | Chemical Formula & Compositional Type | Bioactive Species, Amount (w %) | XRD Results (Nominal) |
|---|---|---|---|
| BC12 | $CaZr_4P_6O_{24}$ (Non-inventive) | 0 w % | Single Phase |
| BC15 | $Ca_{0.9}Ag_{0.2}Zr_4P_6O_{24}$ (II) | $Ag^+$ (2.18) | Single Phase |
| BC16 | $Ca_{0.9}Cu_{0.1}Zr_4P_6O_{24}$ (II) | $Cu^{2+}$ (0.65) | Single Phase |
| BC17 | $Ca_{0.9}Ag_{0.3}Zr_4P_{5.9}Si_{0.1}O_{24}$ (II) | $Ag^+$ (3.23) | Single Phase |
| BC18 | $Ca_{0.9}Cu_{0.15}Zr_4P_{5.9}Si_{0.1}O_{24}$ (II) | $Cu^{2+}$ (0.97) | Single Phase |
| BN2 | $NaZr_2P_3O_{12}$ (Non-inventive) | 0 w % | Single Phase |
| BN6 | $NaAg_{0.1}Zr_2P_{2.9}Si_{0.1}O_{12}$ | $Ag^+$ (2.15) | Single Phase |

For example, for synthesizing a 250 gm. sample of the Type II composition viz. $Ca_{0.9}Ag_{0.2}Zr_4P_6O_{24}$, stoichiometric amounts of the following raw materials—calcium hydroxide [$Ca(OH)_2$], or alternatively, calcium carbonate [$CaCO_3$], silver carbonate [$Ag_2CO_3$], colloidal zirconia ($ZrO_2$), or alternatively, zirconium oxynitrate [$ZrO(NO_3)_2$)]—were added to controlled amounts of deionized water and vigorously mixed using a roll-mill or a paint-shaker. After mixing, the aqueous dispersion of reactant mixture, containing all except the phosphate species, was placed in a large 2000 mL beaker and kept stirred. While being stirred, warm phosphoric acid (at about 35° C. to 40° C.) was added to the reactant mixture slowly. As a result of reaction between the reactant mixture and phosphate species, precipitates begin to form. The precipitation process is typically slightly exothermic and is completed within 10 minutes of starting the reaction.

The resulting precipitates are filtered and dried in an oven between 90° C. and 100° C. for 24 hrs. or until dried. After drying, the precipitates containing the [NZP]-type precursors were placed in a clean ceramic crucible and calcined at a temperature between 900° C. and 1200° C. depending on the intended inventive composition. Up to 6 hrs. of isothermal hold at maximum temperature is needed to complete the formation of crystalline, single-phase [NZP] biocidal composition. The calcined composition which essentially is in a powder form was then subjected to analysis using X-ray diffraction and particle density measurements to verify the crystallinity and purity of the [NZP] phase.

Antimicrobial Testing of Powders of the Ceramic Compositions

Example 2

The general test procedure for antimicrobial testing of the inventive powder samples consisted of the following steps. Phosphate Buffeted Saline (PBS) was diluted to 1× concentration (11.9 mM phosphates, 137 mM sodium chloride and 2.7 mM potassium chloride) to make 400 mL. To 200 mL of the 1×PBS, 2 g nutrient broth was added and dissolved. Test tubes were filled with 9 mL PBS with nutrient broth and about 10 mg of each NZP powder. Each powder was tested in duplicate. Additionally, two test tubes were used without any powder. The last two tubes acted as a positive control. All tubes were capped and autoclaved at 121° C. for 30 minutes. After the test tubes had cooled to room temperature, 1 mL of $10^{-2}$ dilution Munoz XL-1 inoculum was added to each tube with NZP powders as well as the positive control. All solutions were vortexed for 60 seconds to mix before incubating at 32° C. for about 55 hrs. Samples of each tube were then checked for bacteria using an Oxoid dipslide.

Powders of the ionically-substituted, antimicrobially-active [NZP]-type ceramic compositions were tested for antimicrobial properties by Waste Management Research Center (WMRC) in Illinois. Five different inventive compositions of Type (I) and two compositions of Type (TI) were subjected to this testing. Type (I) ceramic compositions were designated as BC12, BC15, BC16, BC17 and BC18. Relevant Type (II) compositions were designated as BN2 and BN6. Of the above ceramic compositions, BC12 (also called BC0) and BN2 (same as BN0) had no bioactive dopants in the [NZP]-type structure, whereas, BC15 through BC18 had slightly different concentrations of bioactive elements, i.e., silver (Ag) and copper (Cu). Table 1 provides details of the designation, chemical formula, weight percent of bioactive element and in each of the single-phase, ceramic compositions.

Figure 3:
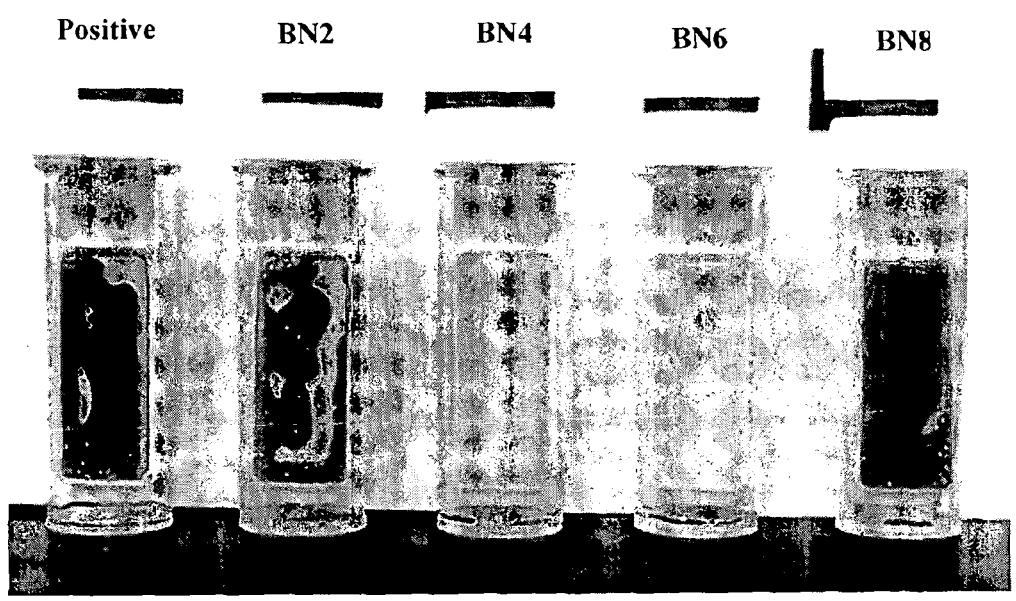
FIG. 3 is a photograph which clearly illustrates the results of an antimicrobial assay test involving some of the inventive biocidal ceramic compositions and their ability to destroy or prevent the growth of *Escherichia Coli* bacteria.

At first, calcined and crystalline powders of the Type (II) compositions were tested using powder concentrations of 1 g/L in a nutrient rich medium. The inventive composition of interest—$NaAg_{0.1}Zr_2P_{2.9}Si_{0.1}O_{12}$—designated as BN6 in Table 1 was estimated to show a log kill effectiveness of greater than 5 and, possibly, up to 8. In contrast, extensive growth was seen in the positive controls and in tubes with undoped ceramic powders BN2 as clearly shown in the picture of FIG. 3.

Next, crystalline powders of the five (5) Type (I) compositions, as in Table 1, were tested for biocidal properties. Surprisingly, initial powder testing of the d-CZP compositions for antimicrobial properties yielded $log_{10}$ microbe reduction numbers that were not conclusive. However, after modification of the powder-testing protocol to use a higher concentration (10 mg/mL instead of 1 mg/mL used for the Type (II) powder testing) of the Type (I) powders in the organism-containing broth, the results showed no bacterial growth in tubes containing powders labeled BC15 and BC17 suggesting pronounced biocidal activity. The estimated $log_{10}$ reduction based on CFU/ml measurements was >4.0 and >5.0, respectively for BC15 and BC17 ceramic compositions. Composition BC18 exhibited some biocidal activity with bacterial counts of $10^5$CFU/mL compared to a positive control which had $10^7$ CFU/mL.

Preparation of Bulk Test Samples of Ceramic Compositions

Example 3

In order to make small tile samples for antimicrobial testing, 125 gms. of each of the calcined powders of the inventive ceramic compositions with substantially, single-phase [NZP] characteristics were dry milled in a paint-shaker with 1 to 2 wt % (based on solids) of PEG-8000 organic solid binder in a clean HDPE (Nalgene) plastic bottle. To facilitate deagglomeration of the calcined composition(s) and to ensure good mixing of the binder with the particles of the ceramic powder, zirconia grinding media weighing roughly four (4) times the mass of the ceramic powder was used and milling was done for at least 15 minutes and up to 30 minutes at a maximum.

The milled ceramic compositions containing the PEG binder were screened dry through a −325 mesh screen to remove any remnant agglomerates. Using roughly 40 gms. of the screened powder, a 2.0 inch (about 5 cm)×2.0 inch (about 5 cm) square tile was formed by uniaxially compressing the powder at 15 MPa in a single-action Carver die press and isostatically-pressing the tile at 210 MPa. For each of the inventive biocidal ceramic composition, two tile samples were die and iso-pressed, followed by sintering at temperatures between 1400° C. and 1500° C. (depending on composition) for 4 hours.

Prior to machining the sintered tiles to appropriate sizes for conducting antimicrobial assay tests at an accredited laboratory, the tile samples were checked for physical integrity and subjected to density testing per ASTM standard. Another key check that was conducted involved observation of color of each of the test tiles. A uniformly white tile (regardless of the bioactive dopant) is usually a good first indicator of having achieved substantially single-phase, crystalline [NZP] compositional characteristics.

Testing of Bulk Samples of Ceramic Compositions

Example 4

A modified AATCC antimicrobial assay was employed by NELSON Labs in Salt Lake City to determine the biocidal properties of the inventive ceramic compositions to be screened. Test samples were die-pressed, sintered, and machined into 1 inch square (about 6.25 cm²) tiles of the respective composition. A proprietary protocol based on inoculating coupons of the test material with the test organism, then determining the percent reduction of the test organism after a specified exposure period was established and followed.

At first, *Salmonella cholerasuis* cultures were grown in soybean casein digest broth (SCDB) media at an incubation temperature of 37.5° C. for between 24 and 48 hours. The bacterial cultures were vortexed thoroughly to remove agglomerates or clumps, and filtered through gauze. The inoculum was also frequently mixed to ensure uniform distribution of challenge. The concentration of the microbial suspensions was adjusted using PEPW to produce a uniform challenge level of approximately $10^6$CFU/mL using visual turbidity.

Prior to test sample inoculation, extraction from uninoculated antimicrobial sample was done in 100 mL aliquots of LETH. To this, approximately 1000 to 10000 CFU of the test organism mix was added and the aliquots plated onto Soybean Casein Digest Agar (SCDA) in triplicate. To confirm the titration of the diluted test organism on the appropriate media, the same volume of inoculum (1000 to 10000 CFU) was added to a 100 mL bottle of LETH. The aliquots were then plated on to SCDA in the same manner. All plates were then incubated at 37.5° C. for 48 to 72 hours. The goal of this procedure was to demonstrate at least 70% recovery or 10 to 100 CFU of the organism.

Roughly 1.0 mL of the challenge organism (about $10^6$ CFU) was placed on the surface of each sample coupon using a pipette. Coupons of all the antimicrobial [NZP]-type compositions as well as untreated baseline materials were tested. The inoculated samples were placed in a closed containment vessel at approximately 37.5° C. for predetermined time(s). At the end of each incubation time interval, the inoculated sample was placed in a flask containing 100 mL of LETH and the flask shaken manually for 1 minute. A plate count (in triplicate) was done using an appropriate aliquot evenly spread on SCDA plates with a sterile bent glass rod (NL1 SOP/MBG/003). This test was done at 0 and 24 hours for the baseline controls and at 24 hours for the antimicrobial materials. For the 24 hr. test, the bacteria laden sample plates were incubated at 37.5° C. for the duration.

Two neutral controls viz. 'gauze' (primary control), which facilitates the natural growth of bacteria under neutral environmental conditions and 'dry wall' (secondary control) were employed for natural bacteria mortality rates. In addition to the two protocol controls, coupons of the baseline undoped compositions were also utilized in the study. For the same testing, as discussed earlier, other positive and negative controls were also utilized. A 100 mL bottle of LETH served as the negative control while the 100 mL bottle of LETH spiked with the challenge organism was the positive control.

Results were calculated in terms of percent reduction of the microbial organism in terms of 'Colony Forming Units' (CFU/sample). The following formula is utilized: $[(C-A)/C] \times 100 = R$ (% Reduction) where 'A' is the number (counts) of organisms recovered from the inoculated test specimens and 'C' is the corresponding number from the inoculated control samples immediately after inoculation (time 't'=0 hrs.). Table 2 below summarizes the results obtained from the antimicrobial testing of the inventive ceramic compositions as compared to passive controls.

TABLE 2

| Sample ID | Exposure Intervals (hr) | Average Control Titer at t = 0 (CFU) | Average Recovered (CFU) | Percent Reduction | Log₁₀ Reduction |
|---|---|---|---|---|---|
| Gauze | 0 | 8.20E+07 | 8.20E+07 | 0 | 0 |
| Control | 24 | 8.20E+07 | 7.00E+08 | −750 | −0.93 |
| Dry Wall | 0 | 8.70E+07 | 8.70E+07 | 0 | 0 |
| Control | 24 | 8.70E+07 | 3.70E+07 | 58 | 0.37 |
| BC0/BC12 | 24 | 8.70E+07 | 2.90E+05 | 99.666 | 2.48 |
| BC15 | 24 | 8.70E+07 | <200 | >99.99977 | >5.64 |
| BC16 | 24 | 8.70E+07 | 6.60E+03 | 99.9924 | 4.12 |
| BC17 | 24 | 8.70E+07 | <200 | >99.99977 | >5.64 |
| BC18 | 24 | 8.70E+07 | <200 | >99.99977 | >5.64 |
| BN0/BN2 | 24 | 8.80E+07 | <200 | >99.99977 | >5.64 |
| BN6 | 24 | 8.80E+07 | <200 | >99.99977 | >5.64 |

Figure 4:
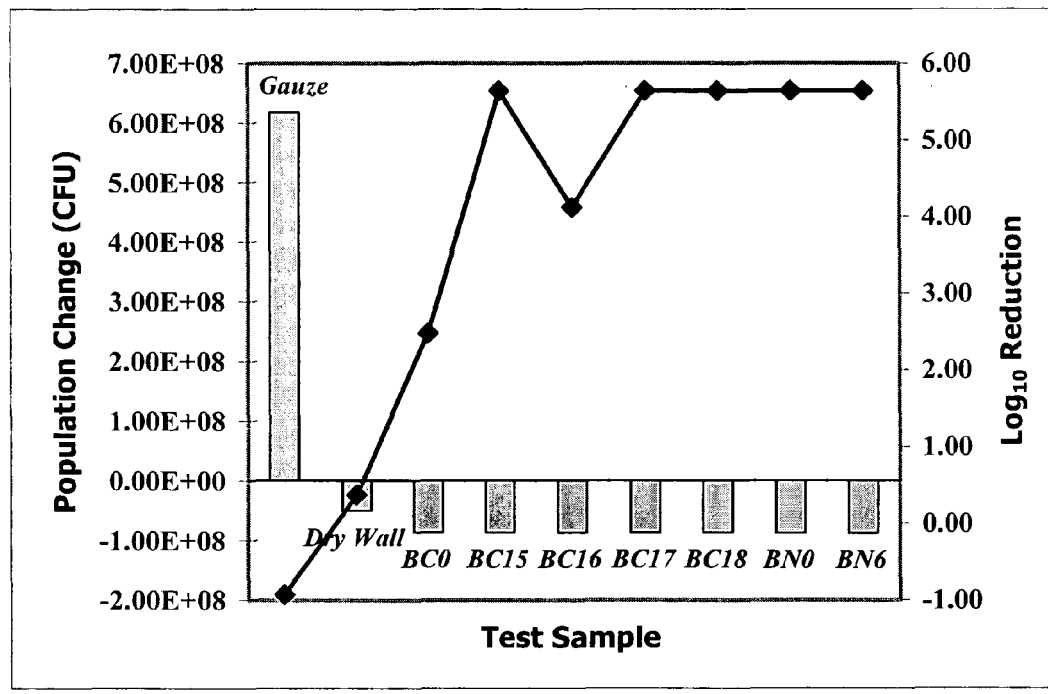
FIG. 4 summarizes the results of antimicrobial testing of small coupon samples of: (a) selected inventive biocidal ceramic compositions; and (b) control samples (gauze and dry wall) and bears clear evidence of the excellent microbe-destroying properties of most of these compositions in contrast to the control samples, which are ineffective.

Almost all bulk test samples (except BC16) from the inventive compositions showed >5.0 log kill values with respect to *Salmonella* bacteria. The test samples had a 30% greater kill rate (99.99977%) than the dry wall, while the gauze control aided bacterial growth which resulted in a population increase of an entire order of magnitude. These results (bacterial population change and log reduction values) have been presented in Table 2 and the antimicrobial activity plot of FIG. 4. The exceptional antimicrobial properties of all but one of the inventive compositions against *Salmonella Choleraesius* and (by scientific deduction) *Escherichia Coli* is, thus, evident. Surprisingly, the undoped [NZP] composition (BN-0) also showed higher than expected levels of biocidal activity arising as a result of its "phosphate" chemistry. Any mechanisms that would explain such high intrinsic activity require further studying.

Example 5

Following the demonstration of the excellent antimicrobial properties of the inventive biocidal ceramic compositions, leaching tests were conducted to evaluate the physical and chemical stability of the same compositions in hot aqueous and mild acid environments. The primary intent was to evaluate resistance to water-enhanced leaching of the bulk tile samples after a 12 hour soak in boiling water (about 100° C.).

A small coupon sample of each of the compositions listed in Table 1 was first weighed and then immersed in boiling water for 12 hours. After the soak period, the coupons were thoroughly dried and then weighed again to determine if there was any weight loss (a manifestation of leaching). As can be inferred from the data in Table 3, most of the tested samples survived the test unscathed with no signs of leaching; while a couple of the samples (BC12 and BN2) exhibited small but measurable weight losses—which was confirmed by the presence of trace amounts of sediments in the water. In conclusion, it can be stated that in spite of the fairly high degree of porosity (33% to 45%) of the leaching test samples, the majority of the [NZP]-type, ceramic compositions are remarkably resistant to leaching in boiling water (H₂O) in spite of their porous nature.

TABLE 3

| Sample Designation | Mass (g) Pre-Test | Mass (g) Post-Test | Density (g/cc) | % Dense | % Weight Loss |
|---|---|---|---|---|---|
| BC12 | 6.53 | 6.51 | 2.018 | 62.48 | 0.31 |
| BC15 | 7.18 | 7.173 | 2.140 | 66.46 | 0.12 |
| BC16 | 7.36 | 7.34 | 1.925 | 61.11 | 0.27 |
| BC17 | 10.19 | 10.18 | 2.117 | 65.78 | 0.09 |
| BC18 | 4.64 | 4.633 | 1.976 | 62.70 | 0.15 |
| BN2 | 7.21 | 7.19 | 1.735 | 54.22 | 0.42 |
| BN6 | 7.36 | 7.36 | 1.808 | 55.90 | 0.00 |

The sample coupons which were subjected to leaching test and, subsequently, dried for about 24 hours under a halogen lamp or under natural sunlight exhibited no color change. Samples of the inventive compositions retained their color regardless of the ambient condition. This not only attests to the chemical-binding of the bioactive species in the single phase, [NZP]-type structure of the inventive compositions but also demonstrates the excellent discoloration resistance inherent to such ceramic formulations.

The present invention may be embodied in other specific forms without departing from its spirit or essential characteristics. The described embodiments are to be considered in all respects only as illustrative and not restrictive. Moreover, the invention disclosed in detail herein can be defined with other claims, including those that will be included in any related non-provisional applications that will be filed during the pendency of this patent application.

What is claimed is:

1. A biocidal ceramic composition for use in microbe-destroying applications, the ceramic composition comprising an effective amount of a bioactive agent that is chemically-bound in a single-phase, crystalline, [NZP]-type structure, the biocidal ceramic composition represented by the following general chemical formula:

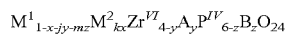

$$M^1{}_{1-x-jy-mz}M^2{}_{kx}Zr^{VI}{}_{4-y}A_yP^{IV}{}_{6-z}B_zO_{24}$$

wherein $M^1$ is at least one divalent alkaline earth cation;
wherein $M^2$ represents ionic-substitution of the $M^1$ sites, wherein $M^2$ is at least one bio-active cation;
wherein $0 < x \leq 1$;
wherein $0 \leq y \leq 4$;
wherein $0 \leq z \leq 6$;
wherein $(jy+mz) < (1-x)$;
wherein k=1 if $M^2$ is a divalent cation;
wherein k=2 if $M^2$ is a monovalent cation;
wherein A represents ionic-substitution of Zr sites,
wherein j=0.5 if A is pentavalent cation;
wherein j=0 if A is tetravalent cation;
wherein j=−0.5 if A is trivalent cation;
wherein B represents ionic-substitution of P sites,
wherein m=0.5 if B is hexavalent cation;
wherein m=0 if B is pentavalent cation;
wherein m=−0.5 if B is tetravalent cation; and
wherein m=−1 if B is trivalent cation.

2. The ceramic composition recited in claim 1, wherein $M^1$ is selected from the group consisting of Mg, Ca, Sr, Ba, and stoichiometric combinations thereof.

3. The ceramic composition as recited in claim 1, wherein $M^2$ is a monovalent cation.

4. The ceramic composition as recited in claim 1, wherein $M^2$ is a divalent cation.

5. The ceramic composition as recited in claim 1, wherein $M^2$ is selected from the group consisting of H, Ag, Cu, Ni, Zn; Mn, Sn, Co, and stoichiometric combinations thereof.

6. The ceramic composition as recited in claim 1, wherein A is selected from the group consisting of $Nb^{5+}$, $Ta^{5+}$, $V^{5+}$, pentavalent lanthanide metals, and stoichiometric combinations thereof.

7. The ceramic composition as recited in claim 1, wherein A is selected from the group consisting of $Ti^{4+}$, $Hf^{4+}$, tetravalent lanthanide metals, and stoichiometric combinations thereof.

8. The ceramic composition as recited in claim 1, wherein A is selected from the group consisting of $Y^{3+}$, $Sc^{3+}$, trivalent lanthanide metals, and stoichiometric combinations thereof.

9. The ceramic composition as recited in claim 1, wherein B is $S^{6+}$.

10. The ceramic composition as recited in claim 1, wherein B is $As^{5+}$.

11. The ceramic composition as recited in claim 1, wherein B is selected from the group, consisting of $Si^{4+}$, $Ge^{4+}$, and stoichiometric combinations thereof.

12. The ceramic composition as recited in claim 1, wherein B is selected from the group consisting of $Al^{3+}$, $B^{3+}$, and stoichiometric combinations thereof.

13. The ceramic composition as recited in claim 1, wherein the ceramic composition is $Ca_{0.9}Ag_{0.2}Zr_4P_6O_{24}$.

14. The ceramic composition recited in claim 1, wherein the bioactive agent is selected from the group consisting of H, Ag, Cu, Ni, Zn, Mn, Sn, Co, and stoichiometric combinations thereof.

15. The ceramic composition as recited in claim 1; wherein the bioactive agent is incorporated into the crystalline, [NZP]-type structure in amounts of about 0.0001 wt % to about 20.0 wt %.

16. The ceramic composition as recited in claim 1, wherein at least 95% of the bioactive agent, based on stoichiometry, is chemically bound in the single-phase, [NZP]-type crystal structure.

17. The ceramic composition as recited in claim 1, wherein at least 99% of the bioactive agent, based on stoichiometry, is chemically bound in the single-phase, [NZP]-type crystal structure.

18. The ceramic composition of claim 1, wherein the composition exhibits log kill rates for *Salmonella cholerasuis* and *Escherichia coli* of at least 2.0 after 24 hours exposure at 37.5° C. and 32° C., respectively.

19. The ceramic composition of claim 1, wherein the composition exhibits log kill rates for *Salmonella cholerasuis* and *Escherichia coli* of up to 6.0 after 24 hours exposure at 37.5° C. and 32° C., respectively.

20. The ceramic composition as recited in claim 1, wherein the ceramic composition has a log-kill rate for harmful microbes of at least 1.0.

21. The ceramic composition as recited in claim 1, wherein the ceramic composition has a log-kill rate for harmful microbes of between about 1.0 to about 7.0.

22. The ceramic composition as recited in claim 1, wherein the ceramic composition exhibits substantially no leaching in boiling water at 100° C. after 12 hours soaking.

23. The ceramic composition as recited in claim 1, wherein the ceramic composition has ultra-low or negative thermal expansion and is dimensionally stable at least up to 1000° C.

24. The ceramic composition as recited in claim 1, wherein the ceramic composition has a melting temperature of at least 1500° C.

25. The ceramic composition as recited in claim 1, wherein the ceramic composition substantially retains its original color when exposed for at least 500 hours to at least one of ambient temperature, boiling water at 100° C., high furnace temperature of at least 1000° C., UV light, visible light, or combinations thereof.

* * * * *